(12) United States Patent
Wobschall

(10) Patent No.: US 7,366,624 B2
(45) Date of Patent: Apr. 29, 2008

(54) MULTI-ELEMENT SMART GAS SENSOR

(75) Inventor: Darold Wobschall, Williamsville, NY (US)

(73) Assignee: Esensors Inc., Amherst, NY (US)

( * ) Notice: Subject to any disclaimer, the term of this patent is extended or adjusted under 35 U.S.C. 154(b) by 0 days.

(21) Appl. No.: 11/145,858

(22) Filed: Jun. 6, 2005

(65) Prior Publication Data

US 2005/0280408 A1    Dec. 22, 2005

Related U.S. Application Data

(60) Provisional application No. 60/577,031, filed on Jun. 4, 2004.

(51) Int. Cl.
  *G01D 18/00* (2006.01)
  *G01R 35/00* (2006.01)
(52) U.S. Cl. .................. 702/91; 702/104; 73/1.06
(58) Field of Classification Search .................. 702/91, 702/104; 73/1.02–1.04, 1.06, 865.9
  See application file for complete search history.

(56) References Cited

U.S. PATENT DOCUMENTS 3,879,717 A * 4/1975 Gruensfelder ............... 340/527
7,031,865 B2 * 4/2006 Bathurst et al. ............. 702/117
2003/0074489 A1 * 4/2003 Steger et al. .................. 710/1
2004/0170360 A1 * 9/2004 Kennedy et al. .............. 385/52

OTHER PUBLICATIONS

We Manufacture Temperature Sensors To Your Specification For Marine Petrochemical Oil And Gas Refinery And General Industries. [online] May 2000 [retrieved on Jul. 23, 2006]. Retrieved from the Internet: URL: http://www.tsspl.com/home.htm.*

* cited by examiner

*Primary Examiner*—Hal Wachsman
*Assistant Examiner*—Mary Catherine Baran
(74) *Attorney, Agent, or Firm*—Hodgson Russ LLP

(57) ABSTRACT

An electronic gas sensor signal conditioner which can automatically adapt to a wide variety of commercial off-the-shelf sensors and provide a digital output in a standard, easily used format. The signal conditioner has analog and digital sections. The analog section includes a sensor excitation sub-section and a signal amplification sub-section. The digital section comprises a microcontroller and controls the analog section. The digital section also converts the signal from the analog section into digital form, reads the sensor TEDS (Transducer Electronic Data Sheet), applies calibration constants and converts the signal into a standard, easily readable digital format.

16 Claims, 23 Drawing Sheets

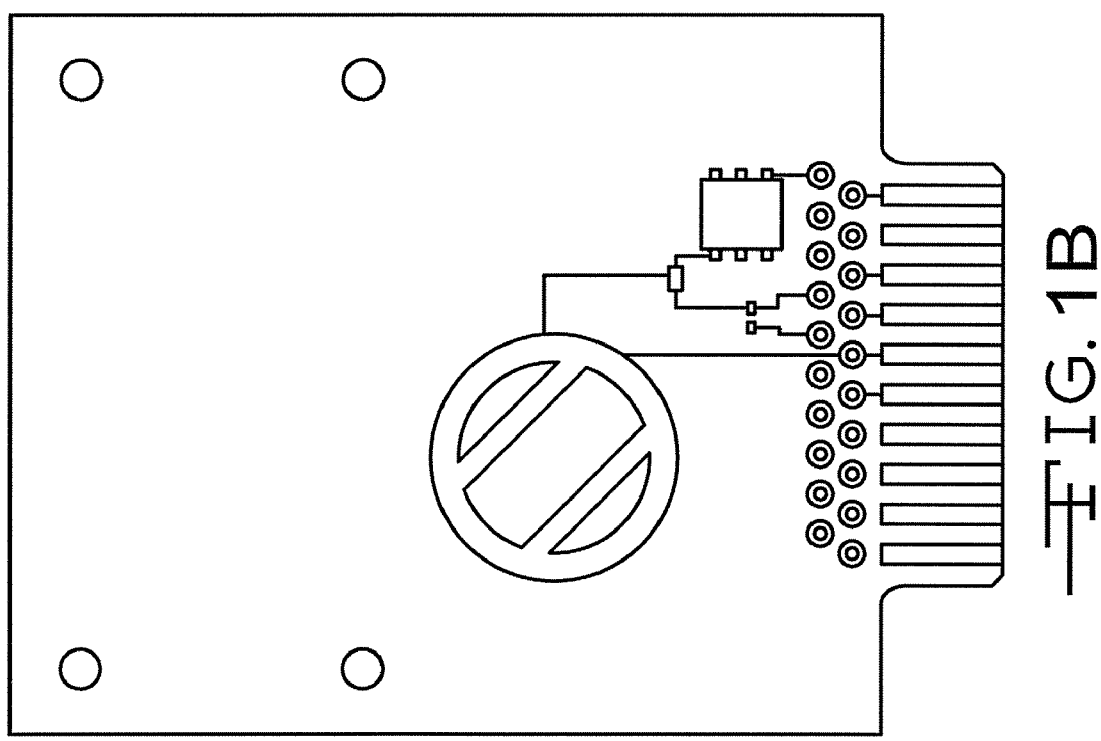

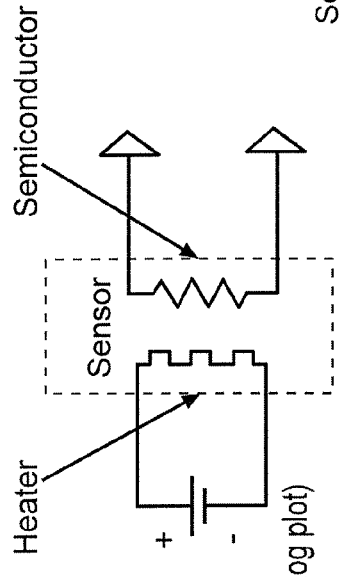
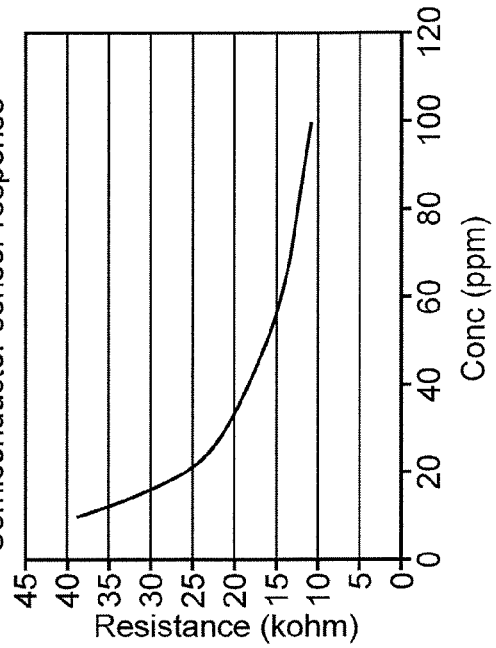
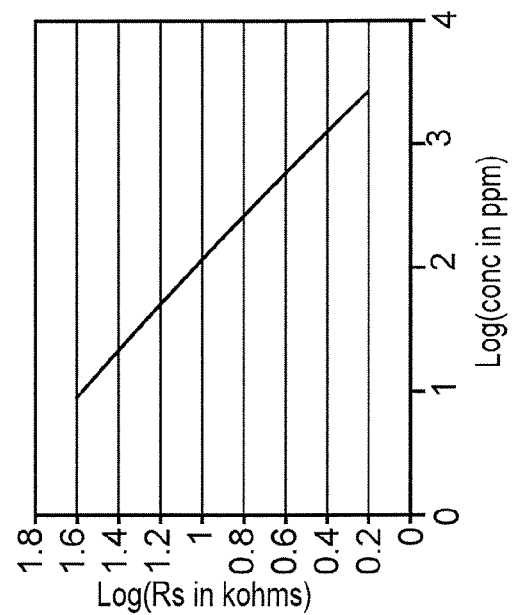
FIG. 2AB
FIG. 2AA

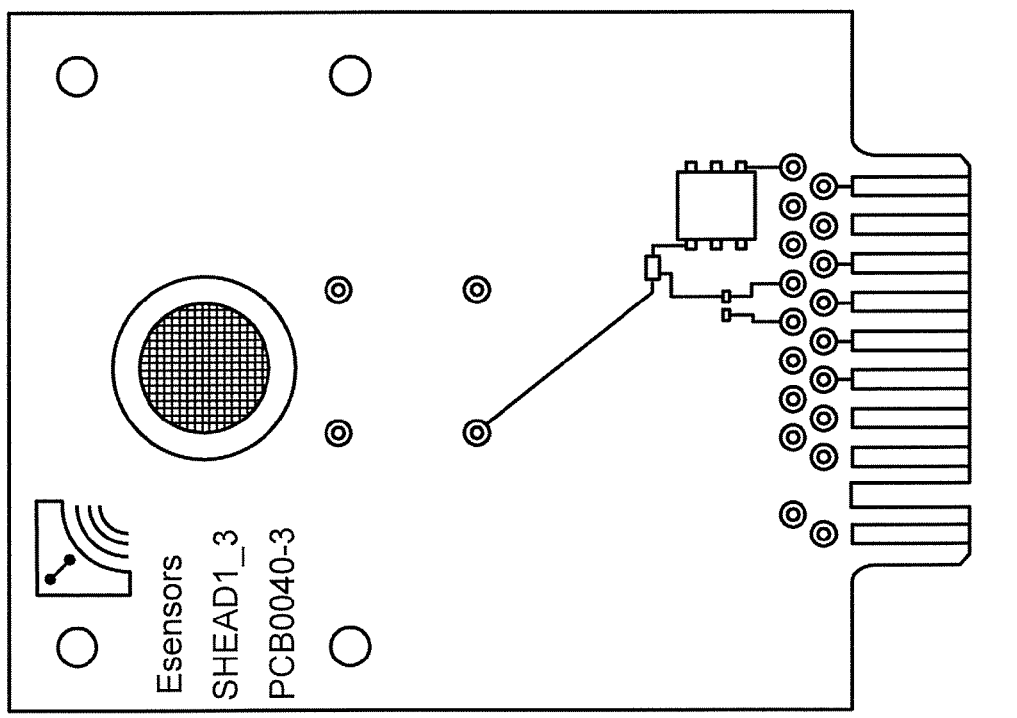

Solid Electrolyte Gas Sensor

- Similar to semiconductor gas sensor but has voltage output
- Heater (5v @ 11.5 ohms)
- Has thermistor for temperature control
- Vsen increases 50 mv per factor of 10 change in gas conc
  (220 to 490 mv at 350 ppm)
- Requires hi-Z amplifier
- Examples: Figaro TGS4160 ($CO_2$) or Oxygen (zerconia)
- Periodic re-zoning desirable

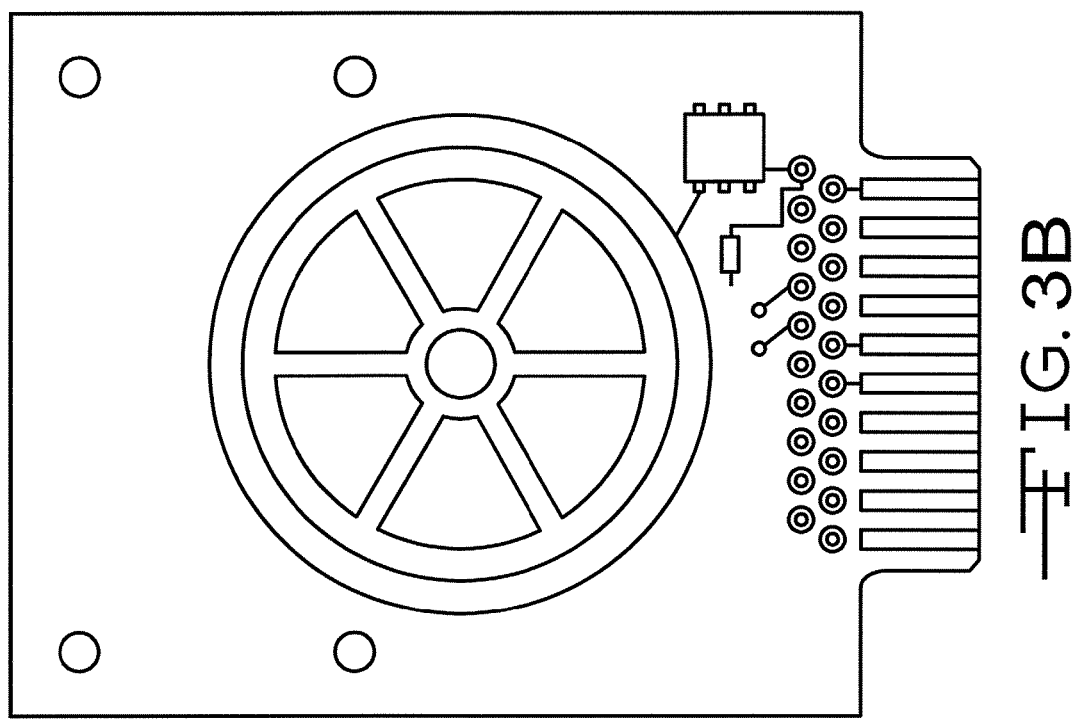

City Tech Ltd - Toxic Gas Sensors

Infra-red Principle

- Some gases absorb light at paticular IR wavelengths
- $I/Io = e^{-Ax}$
  where $I/Io$ is light absorbed during transmission, $x$ is path length and $A$ is absorption coef. at specific wavelength
- Transmission filters select specific wavelength bands
- A is proportional to gas concentration
- IR sensors reproducible but not sensitive (need high conc or long paths)

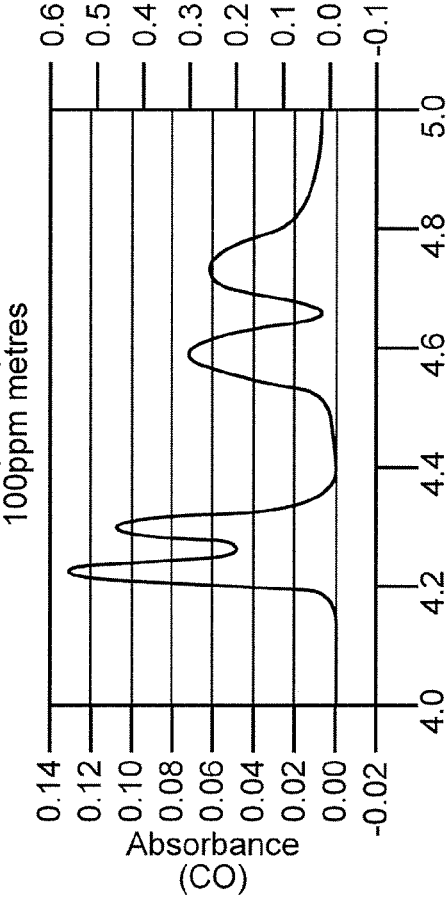

FIG. 5A

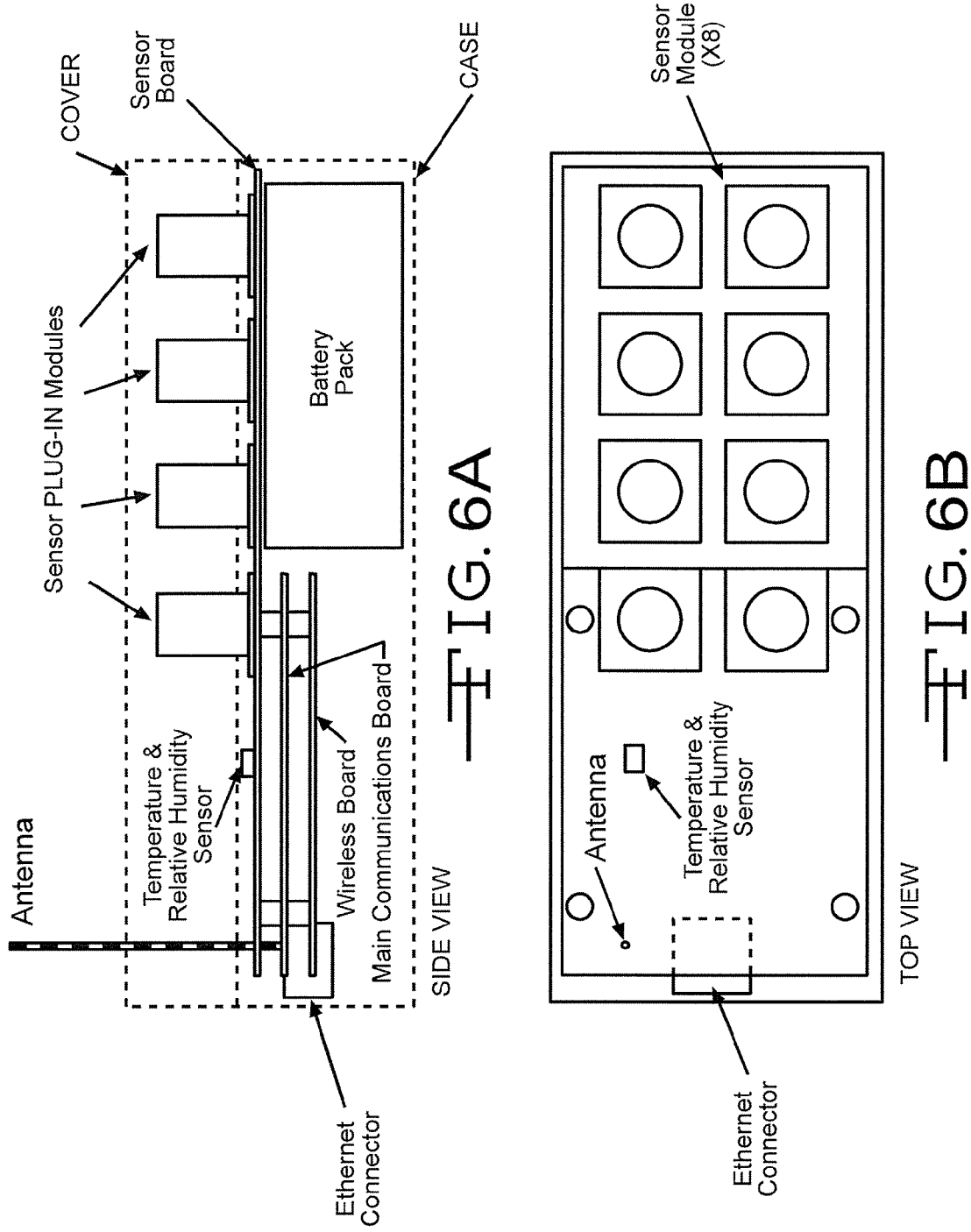

Photo-ionization

- High energy UV photons (> 3ev or <300 um) will ionize some gases (e.g. toluene, trichloroethyene) but not others (e.g. air, methane)
- Ions collected by e-field produce a current proportional to gas conc
- Sensitive (< 1 ppm) but not selective
- Special UV lamps costly and have limited life (also high power)

SAW and vibrating beam

- Surface acoustic wave (SAW) travel from transmitter to receivef on substrate surface
- Velocity depends on surface mass which is effected by absorbed gases
- Positive feedback produces oscillation at frequency which depends on sound velocity and thus gas concentration

SAW and vibrating beam

- Surface acoustic wave (SAW) travel from transmitter to receivef on substrate surface
- Velocity depends on surface mass which is effected by absorbed gases
- Positive feedback produces oscillation at frequency which depends on sound velocity and thus gas concentration

SAW and vibrating beam continued

- Usually used in pairs (one not exposed to gas) and difference (beat frequency) measured
- Moderate sensitivity and selectivity
- Vibrating beam type (usually quartz) resonance frequency varies with mass loading and thus gas concentration.
- Can be small and low cost
- Few commercial products available.

Capacitive

- Dielectric constant of polymer increase with absorbed gas such as water vapor (K is 80 for water, 2-3 for polymer)
- Typicall C increase by 10-30% as relative humidity (RH) varies from 0 to 100%.

MULTI-ELEMENT SMART GAS SENSOR

CROSS REFERENCE TO A RELATED APPLICATION

Applicant claims priority based on Provision Application No. 60/577,031 filed Jun. 4, 2004 entitled "Multi-Element Smart Gas Sensor" which is incorporated by reference.

BACKGROUND OF THE INVENTION

This invention relates to the art of electrically-operated gas sensors, and more particularly to a new and improved signal conditioner for such sensors.

Electronic chemical gas sensors are used both for long-term or chronic monitoring of environmental gases, especially in buildings, and to provide warnings of acute gas build-up due to a chemical incident or attack. These sensors may involve a wide range of technologies and the supporting electronics, or signal conditioner, must match the technology. Commercial gas monitors typically have a small, fixed number of sensors for specific gases (e.g. oxygen or chlorine) and these are often factory-installed and difficult to change.

In emergency situations, the type of gas sensor required may not be known until the incidence occurs. For these situations, it would be desirable to have gas sensors available which are "plug-and-play" or automatically configurable. The multi-element smart gas sensor invention described herein is intended to allow commercial, off-the-shelf gas sensors to be implemented in portable gas monitors and provide this automatic configuration.

Another reason for flexibility in a monitor's capacity to use different sensor technologies is that sensors are not interchangeable as are most electronic components. Some sensors are made only in one factory (world-wide) and are in short supply. Also very often the individual responses and calibrations differ.

A standard format for digital smart sensors (IEEE 1451.4 or Dot 4) has been developed by a national/international committee sponsored by NIST. A major purpose is to facilitate plug-and-play of sensors. One aspect is the Transducer Electronic Data Sheet (TEDS) which allows sensor configurations and calibration information to be stored (in digital form) with a sensor, along with its ID. The TEDS feature of this open standard is used in this invention.

SUMMARY OF THE INVENTION

The invention provides an electronic gas sensor signal conditioner which can automatically adapt to a wide variety of commercial off-the-shelf sensors and provide a digital output in a standard, easily used format. The signal conditioner has analog and digital sections. The analog section includes a sensor excitation sub-section and a signal amplification sub-section. The digital section comprises a microcontroller and controls the analog section. The digital section also converts the signal from the analog section into digital form, reads the sensor TEDS (Transducer Electronic Data Sheet), applies calibration constants and converts the signal into a standard, easily readable digital format.

The foregoing and additional advantages and characterizing features of the invention will become clearly apparent upon a reading of the ensuing detailed description together with the included drawing.

BRIEF DESCRIPTION OF THE DRAWINGS

FIG. 1B illustrates a first shape and electrical connection of an electronic gas sensor;
FIGS. 2AA and 2AB are graphs illustrating resistive responses of solid state gas sensors;
FIG. 2B illustrates a second shape and electrical connection of an electronic gas sensor;
FIG. 3B illustrates a first shape and electrical connection of an electronic gas sensor;
FIG. 5A is a graph illustrating a gas sensor operating on the infra-red principle;
FIGS. 6A and 6B are side elevational and top plan views, respectively, of a multi-element gas monitor system.

The following detailed description is in such full, clear, concise and exact terms as to enable any person skilled in the art to which it pertains, or with which it is most nearly connected, to make and use the invention.

DETAILED DESCRIPTION OF THE INVENTION

Figure 1:
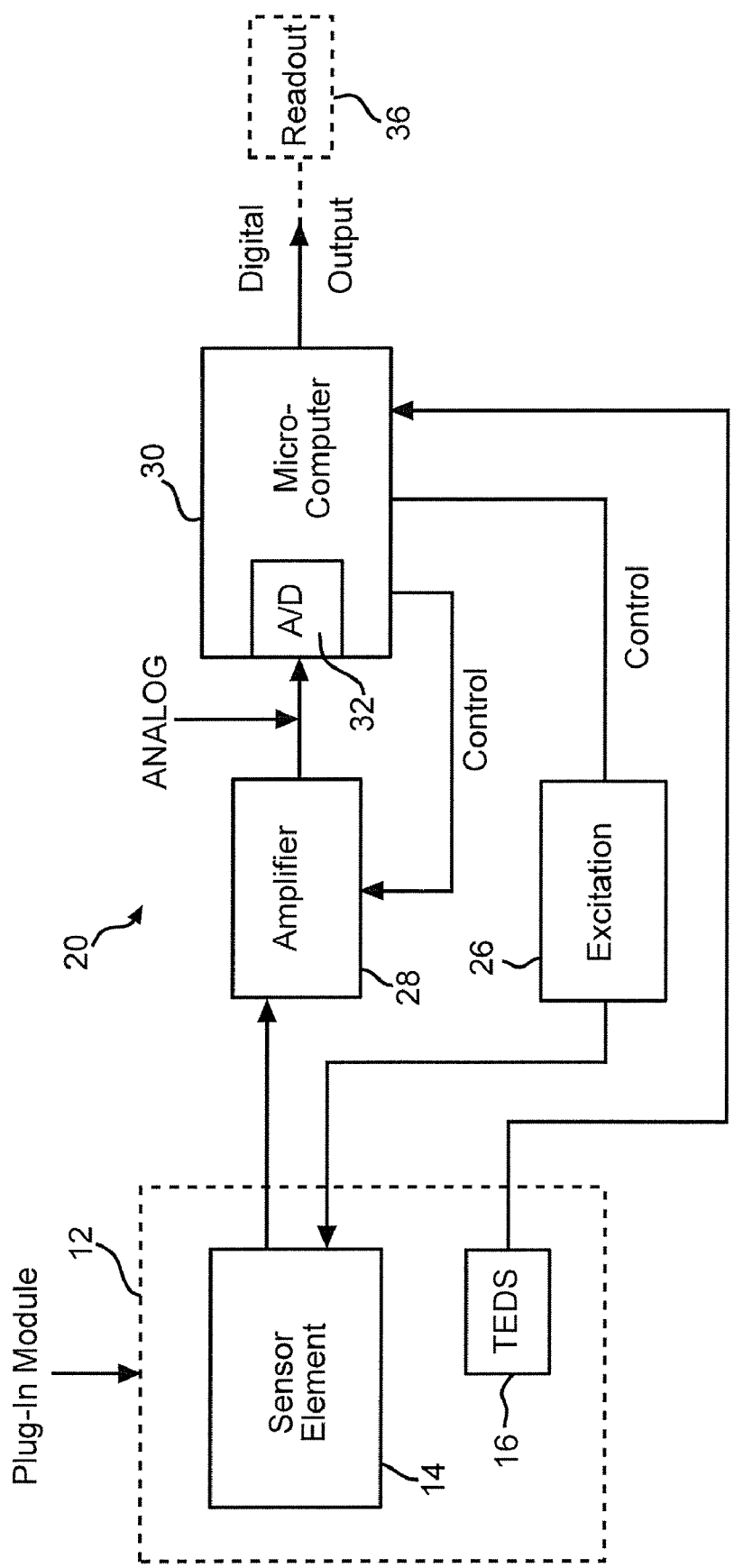
FIG. 1 is a block diagram of the multi-element smart gas sensor according to the invention.
Figure 1A:
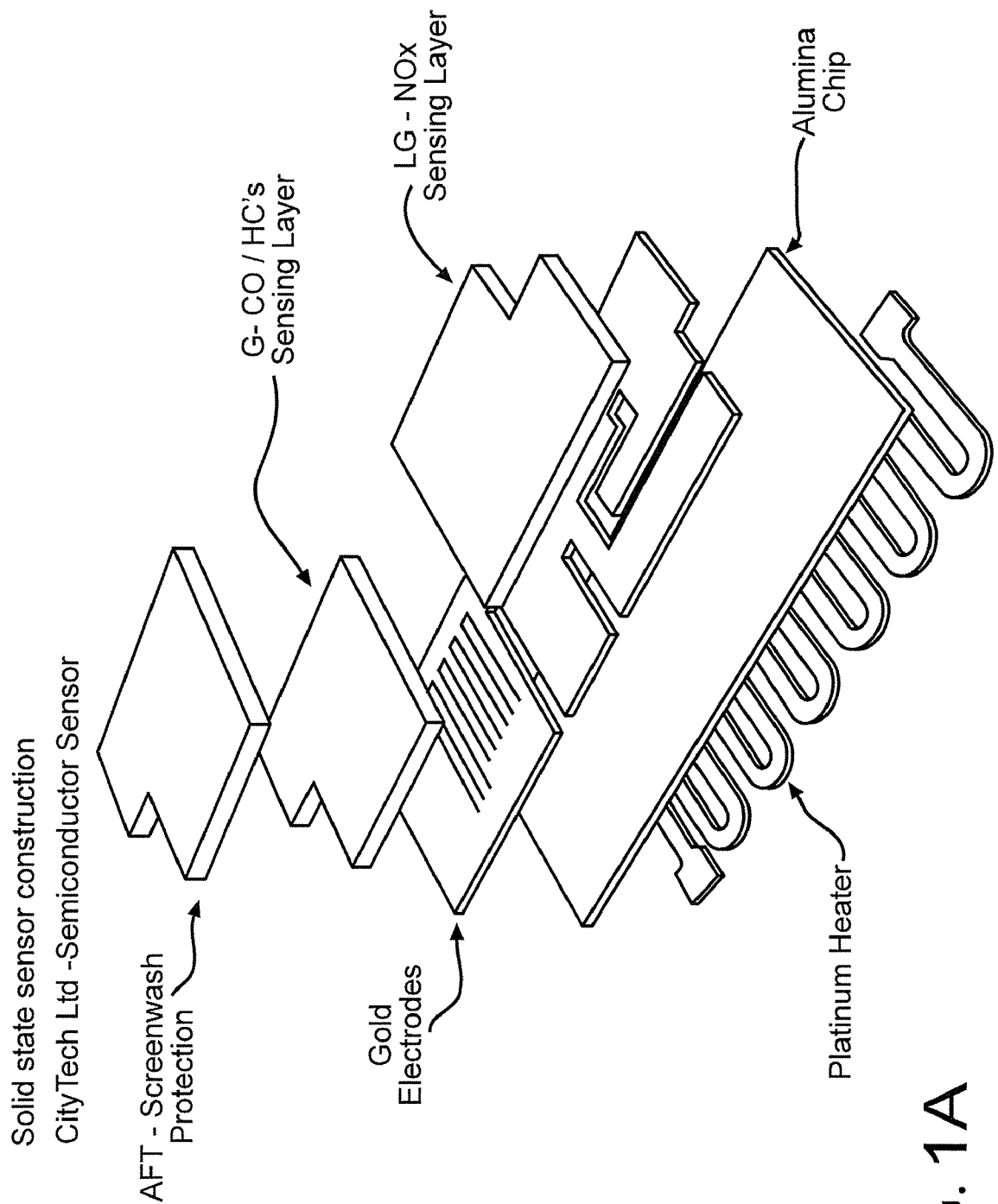
FIG. 1A is a developed diagrammatic view of a solid state gas sensor.

The invention is an electronic sensor signal conditioner which can automatically adapt to a wide variety of commercial off-the-shelf sensors and provide a digital output in a standard easily used format. As shown in FIG. 1 the electronic gas sensor is in the form of a plug-in module 12 containing a sensor element 14 and a component 16 in which sensor specification information is stored in digital form. As will be described in detail presently, component 16 represents the Transducer Electronic Data Sheet (TEDS).

The signal conditioner 20 of the invention has analog and digital sections. The analog section comprises a sensor excitation sub-section 26 and a signal amplification sub-section 28. The analog sections are controlled by the digital section comprising a microcontroller 30 including A/D converter 32. The digital section also converts the analog signal into a digital form, reads the TEDS, applied calibration constants, and converts the signal into a standard, easily readable digital format in an appropriate readout or display component 36.

Figure 2:
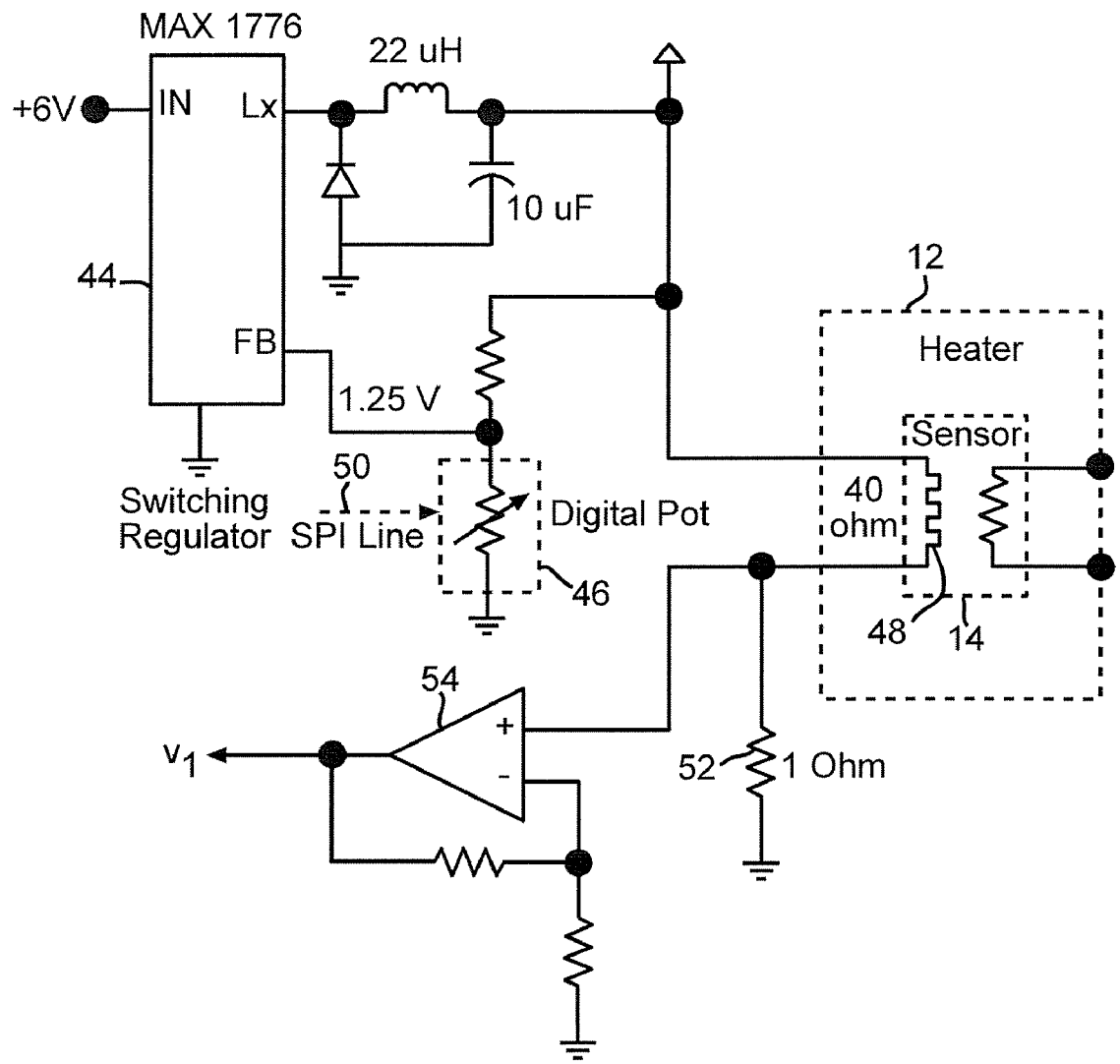
FIG. 2 is a schematic circuit diagram for the sensor heater supply in the arrangement of FIG. 1.

A review of commercial sensor technology is given in Appendix A. Excitation or voltage current supply requirements for these sensors fall into two groups: [1]heaters 1to 5 v, up to 200 ma) and/or [2]precision reference voltages (0.1 to 2.5 v). To supply the first group, a switching regulator 44 (dc-to-dc supply) with feedback determined by a digital potentiometer 46 is used as shown in FIG. 2. It produces the required voltage for the sensor heater 48 between 1 and 5 volts (10-200 ma). Adjustment of the voltage is done through a serial digital (SPI) signal on line 50 from the microcontroller 30. The heater current is measured by 1-ohm shunt resistor 52 and amplifier 54 so that the heater current can be controlled to a specific set point. The SPI input on line 50 to digital potentiometer 46 changes the voltage, the configuration of regulator 44 changes the current output on Lx, and these voltage and current changes in turn can have the effect of changing the sensor resistance.

Figure 3:
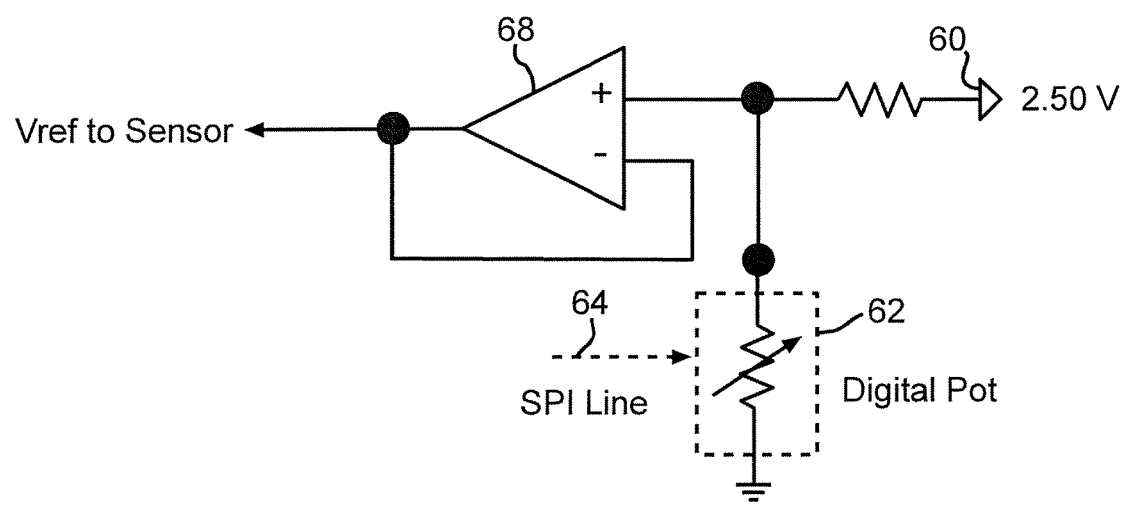
FIG. 3 is a schematic circuit diagram of a sensor excitation voltage source in the arrangement of FIG. 1.
Figure 3A:
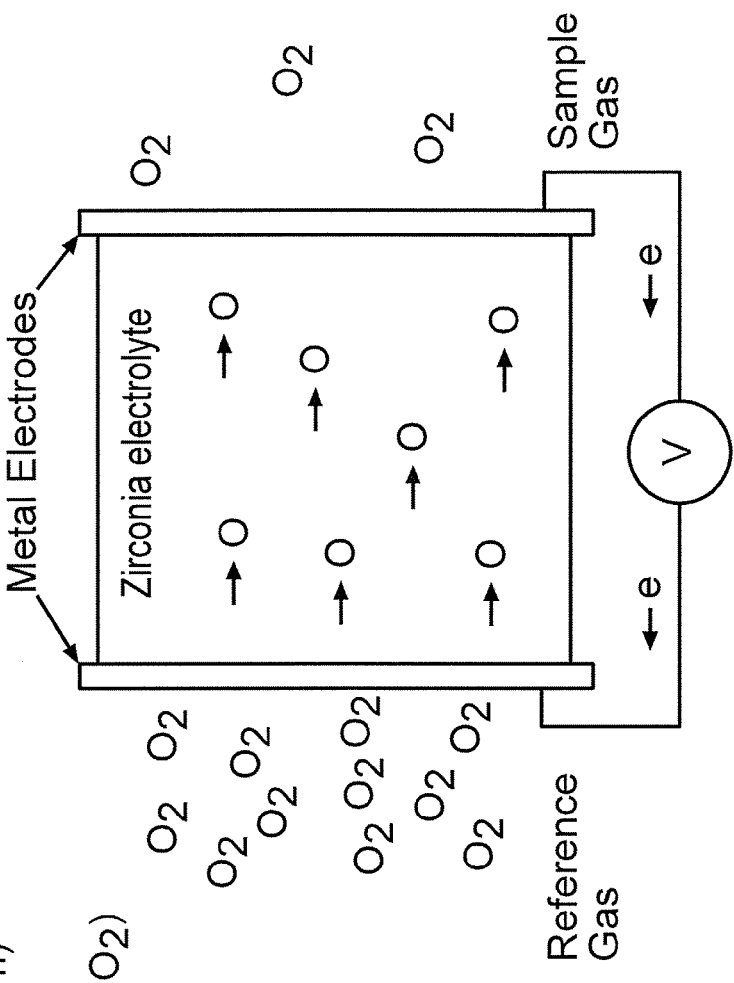
FIG. 3A is a diagrammatic view illustrating a solid electrolyte gas sensor.

For sensors requiring a precision voltage source as the excitation, the voltage from a precision 2.5-volt reference 60 is passed through a digitally controlled attenuation provided by a digital potentiometer 62 adjusted through a serial digital (SPI) signal on line 64 from the microcontroller 30 as shown in FIG. 3. A unity-gain amplifier 68 provides sufficient current capacity (up to 10 ma) for all known sensors.

Figure 4:
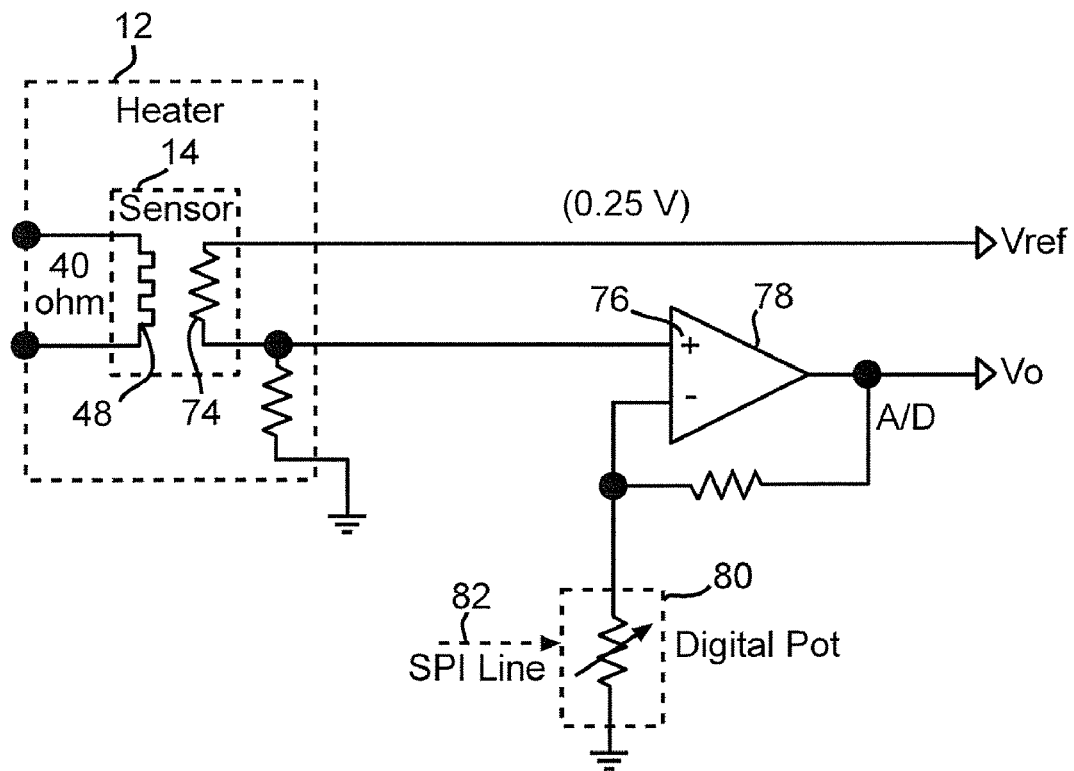
FIG. 4 is a schematic circuit diagram of a sensor signal amplifier in the arrangement of FIG. 1.
Figure 4:
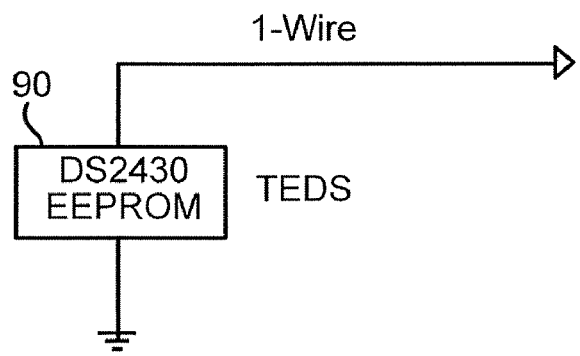

All reviewed sensors have a voltage output with most, but not all, requiring a specified load resistor. The amplifier section shown in FIG. 4 brings the voltage level up to that required by the analog-to-voltage converted in the digital section. The output from sensor component 74 is applied to an input 76 of amplifier 78. Because some sensors are high impedance, the amplifier must have a low input bias current. Many sensors require a stable DC baseline or zero and therefore the amplifier must also have a low input offset voltage. Amplifier 78 is controlled by a digital potentiometer 80 adjusted through a serial digital signal on line 82 from microcontroller 30.

Figure 5:
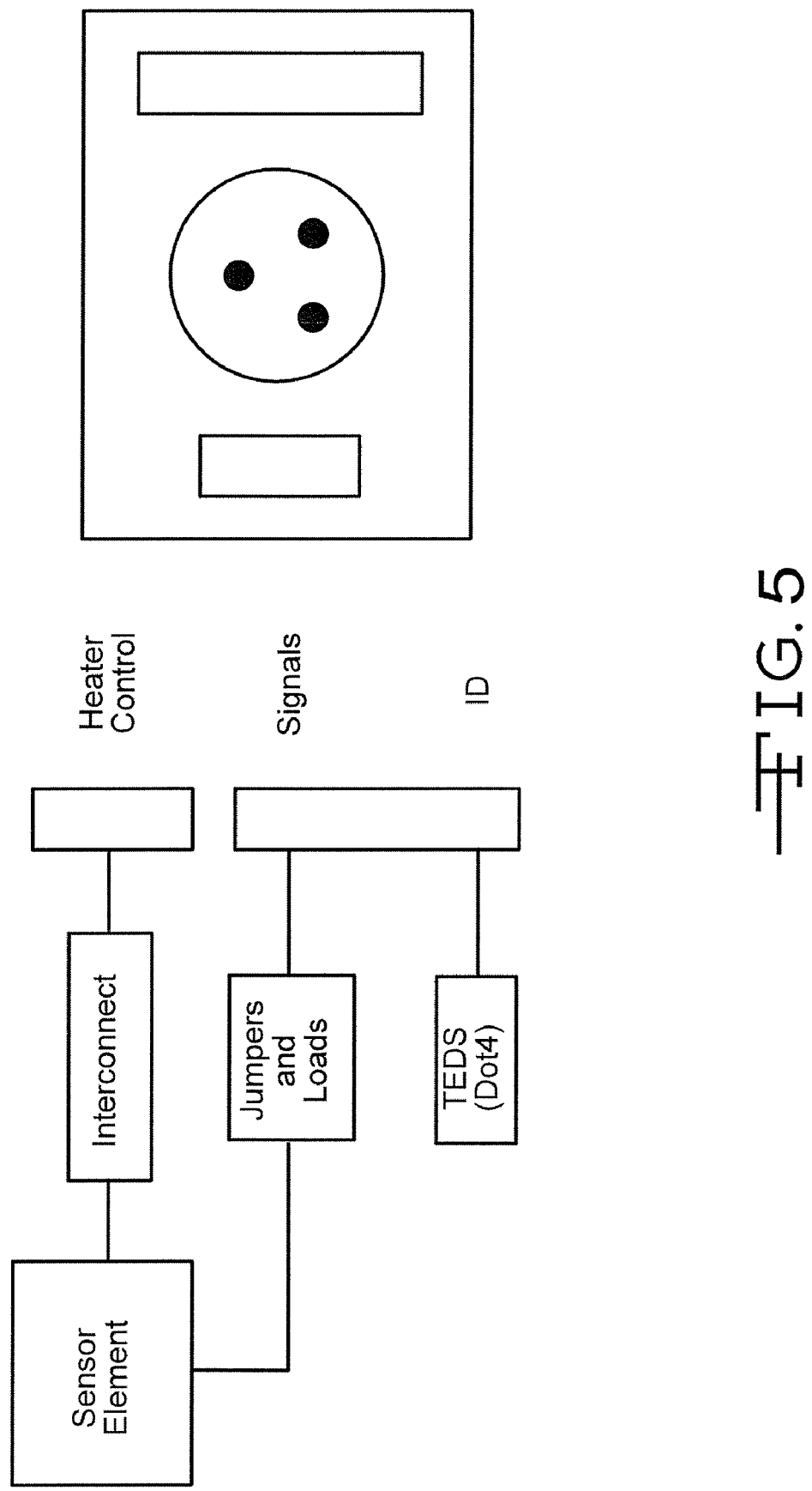
FIG. 5 is a diagrammatic view illustrating sensor module examples.

Sensors from different manufacturers made with different technologies have diverse shapes and electrical connections as shown in Appendix B. To accommodate these differences, sensor modules specific to the sensor shown in FIG. 5 but which will plug into a common signal conditioner connector, are made as shown in FIG. 6.

This approach allows a single connector or plus to be used for all sensor modules. In addition, the required load resistors or other circuit elements specific to the sensor be added.

An essential part of the sensor module is the TEDS. It uses the IEEE 1451.4 (Dot 4) protocol based on a 1-wire flash memory (EEPROM) designated 90 in FIG. 4. The TEDS provides the manufacturer, model, and serial number as well as the calibration constants for the specific sensor. When the sensor module 12 is plugged in, the microcontroller 30 reads the TEDS and reconfigures the excitation 26 and amplifier 28 sections for the signal conditioner to match. Additionally sensitivity and zero offset constants are provided for software conversion algorithms.

Figure 7:
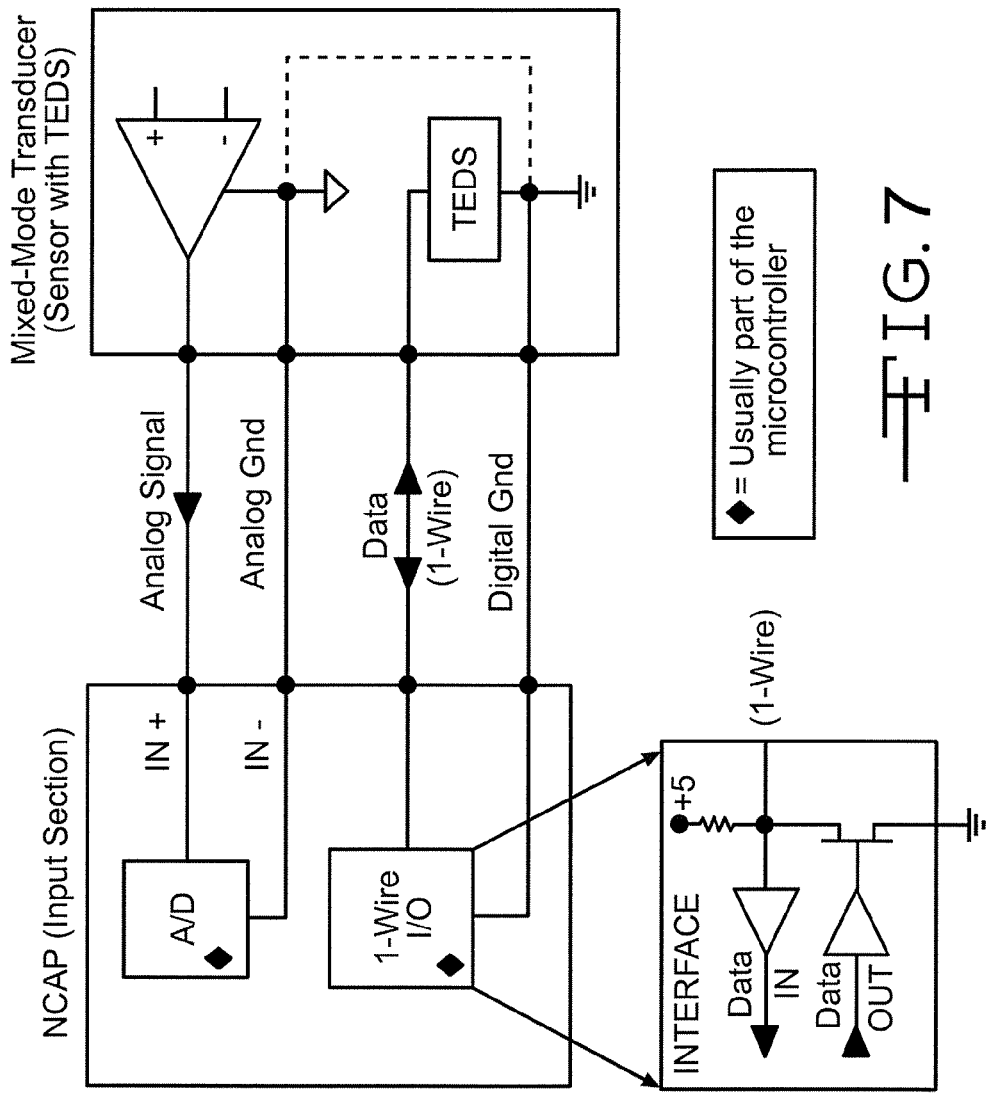
FIG. 7 is a schematic diagram illustrating IEEE 1451.4 (Dot 4) interface.
Figure 8:
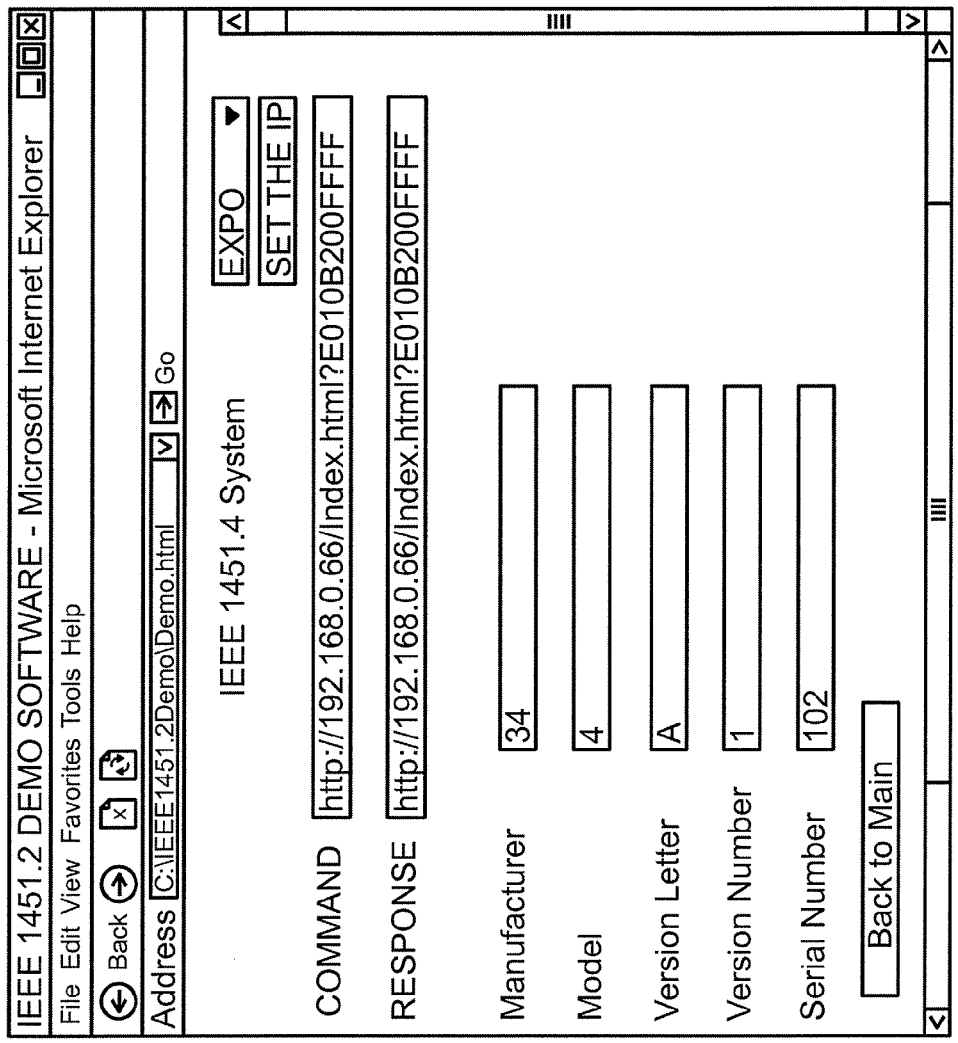
FIG. 8 is a computer screen print-out illustrating the basic transducer electronic data sheet (TEDS)
Figure 8A:
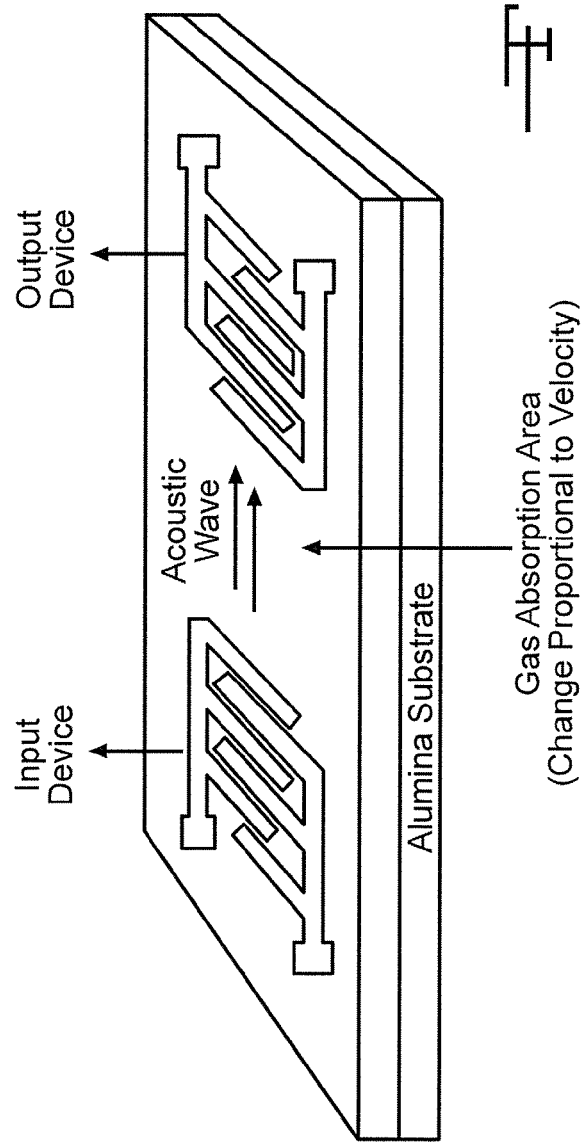
FIG. 8A is a diagrammatic view of a surface acoustic wave and vibrating beam type gas sensor.

The foregoing is illustrated further by the presentation in FIG. 7 of the IEEE 1451.4 (Dot 4) interface and the computer screen print-out of FIG. 8 showing the basic transducer electronic data sheet (TEDS). The following is a summary of IEEE p 1451.2 TEDS Blocks:

| Machine Readable | Human Readable |
|---|---|
| Meta-TEDS (mandatory) | Meta-ID TEDS |
| Channel TEDS (mandatory) | Channel-ID TEDS |
| Calibration | Calibration-ID TEDS |
| Physical Layer Meta (proposed) | Application Specific End Users' Application-Specific TEDS |
| Physical Layer Channel (proposed) | Future Extensions Industry Extension TEDS |

Note:
One TEDS per channel for Channel and Calibration

New Tuples Format TEDS Approved by Dot2 Working Group

Advantages of the IEEE Standard are the following:

Continuing network interface and microcontroller cost reductions have made interface more attractive.

The sensor industry is closer to recognizing the necessity for a sensor network standard.

The general concept of the IEEE 1451 approach, especially TEDS, is supported by many.

Working groups are addressing the dot2 problems and expanding the standard via dot3, dot4, and dot5.

The IEEE 1451.4 (Dot4) Interface is shown in the schematic diagram of FIG. 7. FIG. 8 shows a computer screen printout illustrating the basic transducer electronic data sheet (TEDS). Dot2 to Dot4 TEDS conversion involves the following:

Dot4 TEDS read over 1-wire (specific sensor head).

Contains standard TEDS and special (manufacturer specific) TEDS.

Special head configuration data used for signal conditioner setup.

A/D data read in and converted to floating point (Dot2 option).

Calibration data from Dot4 TEDS used to convert to engineering units.

Data from Dot4 standard TEDS used to prepare tuples style Dot2 (Dot0) TEDS (Meta, Channel, Meta-ID, and Channel ID).

Parameters (fields) not in Dot4 TEDS inserted into Dot2 TEDS.

UUID or Universal Unique Identification (10 bytes) consists of 6-byte Dot4 TEDS as the least significant+4 bytes (FFFF0000h), which will not occur using the specified Dot2 formula.

Figure 9:
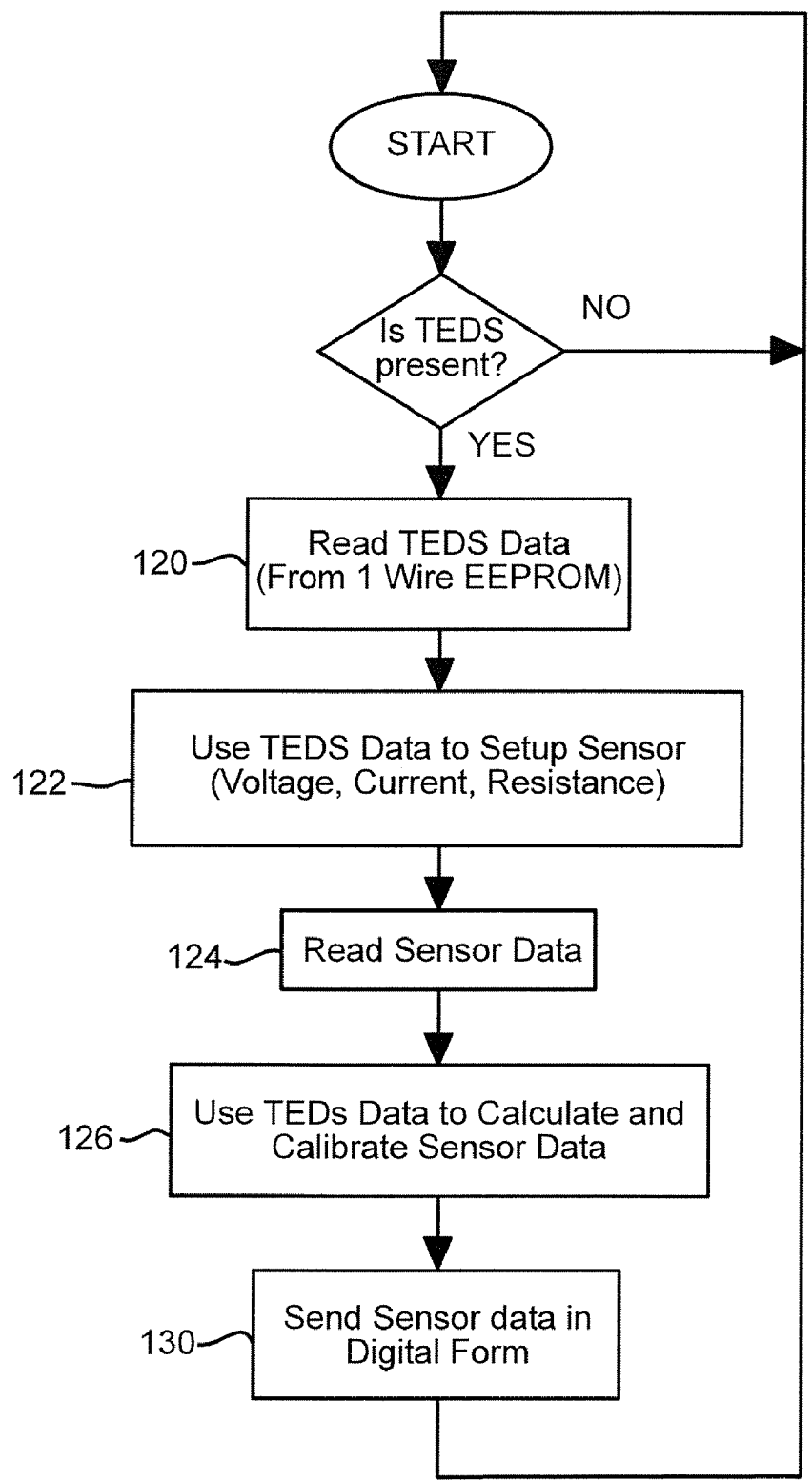
FIG. 9 is a flow chart illustrating the method of the invention.
Figure 9A:
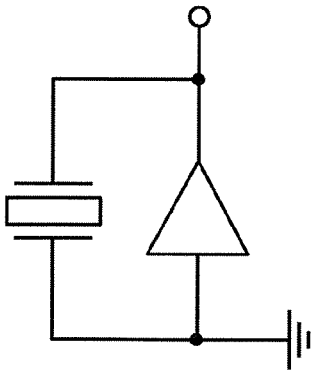
FIG. 9A is a schematic diagram of the equivalent circuit of the sensor of FIG. 8A.
Figure 9A:
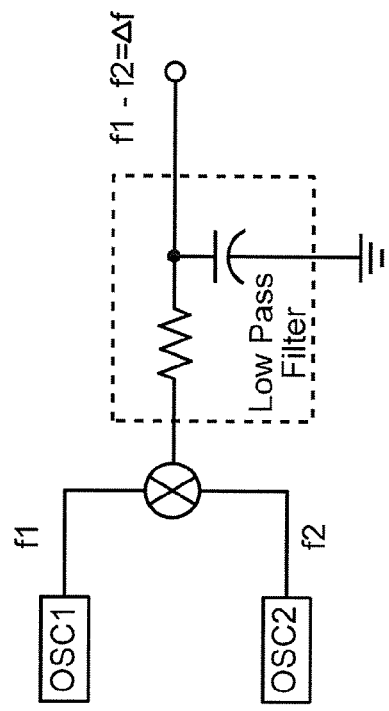
Figure 10A:
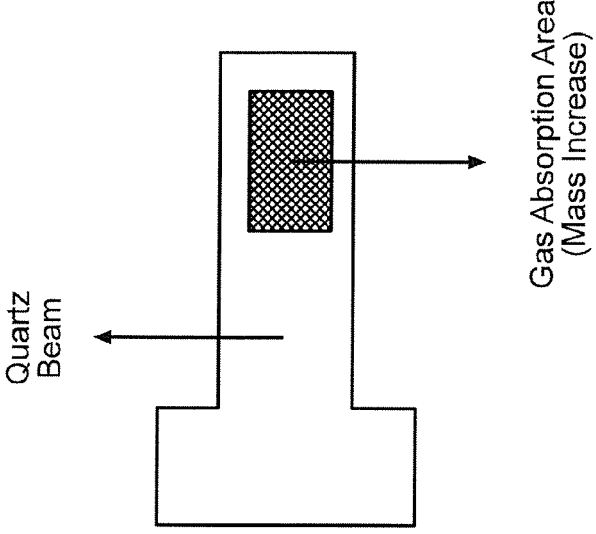
FIG. 10A is a diagrammatic view further illustrating the sensor of FIG. 8A.

The method of the invention, centered around the operation of microcontroller 30, is illustrated in FIG. 9. Operations 120 and 122 involve reading and using TEDS data, sensor data is read in operation 124, the sensor data is calculated and calibrated using TEDS data in operation 126 and the resulting sensor data is provided in digital form by operation 130 and can be utilized, for example, by the readout component 36 in FIG. 1.

While an embodiment of the invention has been described in detail, that has been done for the purpose of illustration, not limitation.

Appendix A

Gas sensors employ a wide variety of technologies. Those technologies include semiconductor-resistive, semi-conductor-voltage, amperometric, catalytic, infrared, photo-ionization, fluorescent, surface acoustic wave (SAW) and vibrating beam, capacitive and others. Any particular gas sensor may include one or more of the foregoing technologies.

DETAILED DESCRIPTION

Solid state or semiconductor type gas sensors have the following characteristics:
  Based on Tin Oxide ($SnO_2$) or similar metal oxide semiconductors.
  Surface reaction with ambient gases when hot (350-500° C.).
  Heater (e.g. 4 v @100 mA) heats substrate.
  Adsorbed gas reduces grain-boundary potential barrier and thus increases conductivity (decreases resistance).
  Delta-R is a function (approx. log or square root) of gas concentration (ppm).
  Resistance also decreases with temperature so temperature control needed for zero stability.
  These are illustrated further in FIGS. 1A-3A.

Figure 4A:
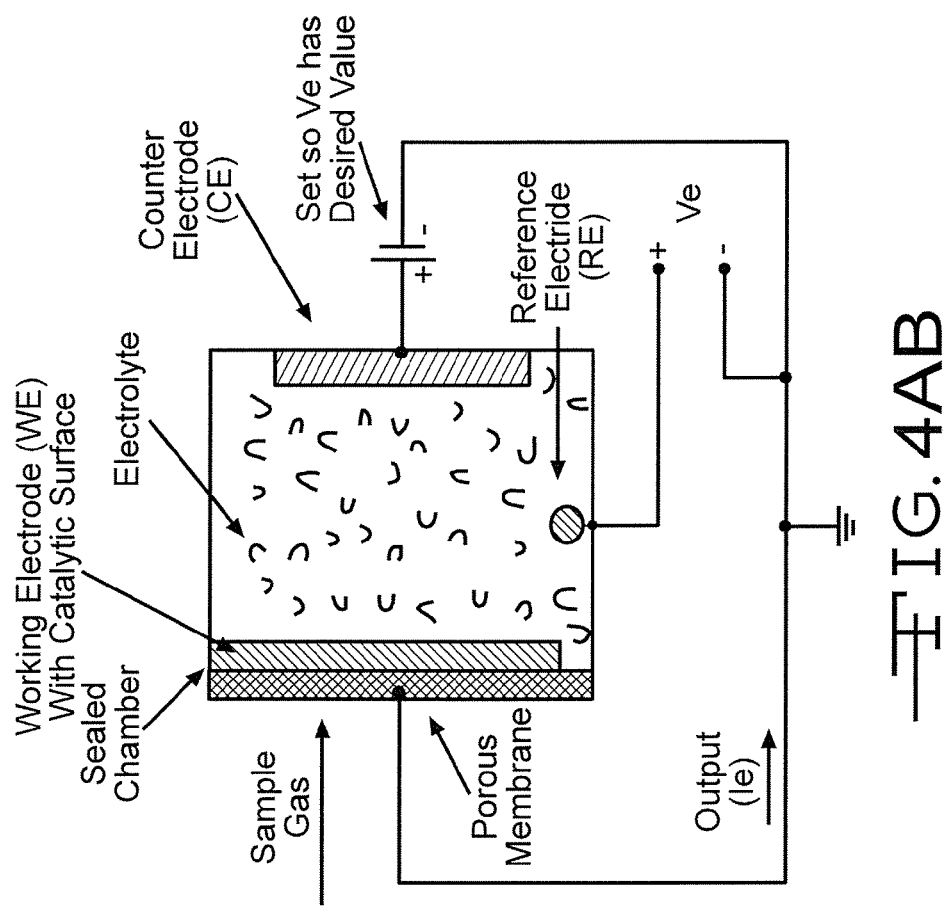
FIGS. 4AA and 4AB are diagrammatic views illustrating constructions of amperometric type gas sensors.
Figure 4A:
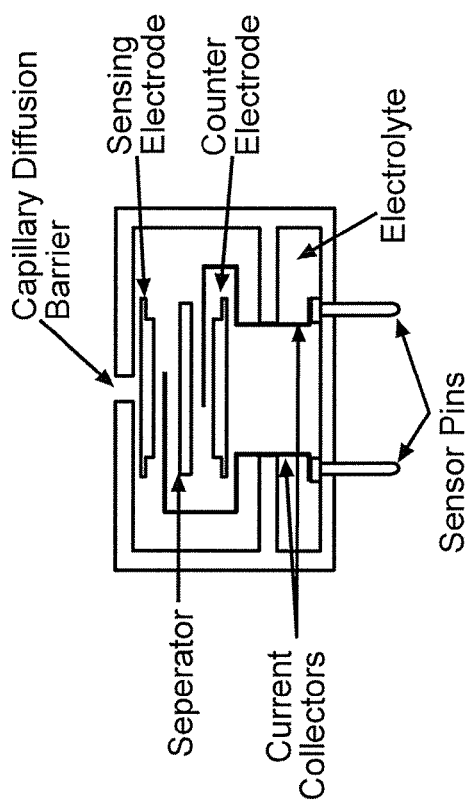

Amperometric type gas sensors have the following characteristics:
  Chemical reaction involving gas releases electrons at electrode (electrolysis reaction).
  Example: $\frac{1}{2}O_2 + H_2O + 2e^- \rightarrow 2OH^-$
  Gas is dissolved in electrolyte (e.g. $H_2O$).
  Reaction is reversible so number of electrons released is proportional to gas concentration (gas conc. in electrolyte is proportional to partial pressure of gas in air).
  Reaction occurs at specific applied voltage (e.g. 0.55 volts).
  Sensor current output is proportional to gas conc. (ppm).
  These are illustrated in FIGS. 4AA and 4AB.

Figure 6C:
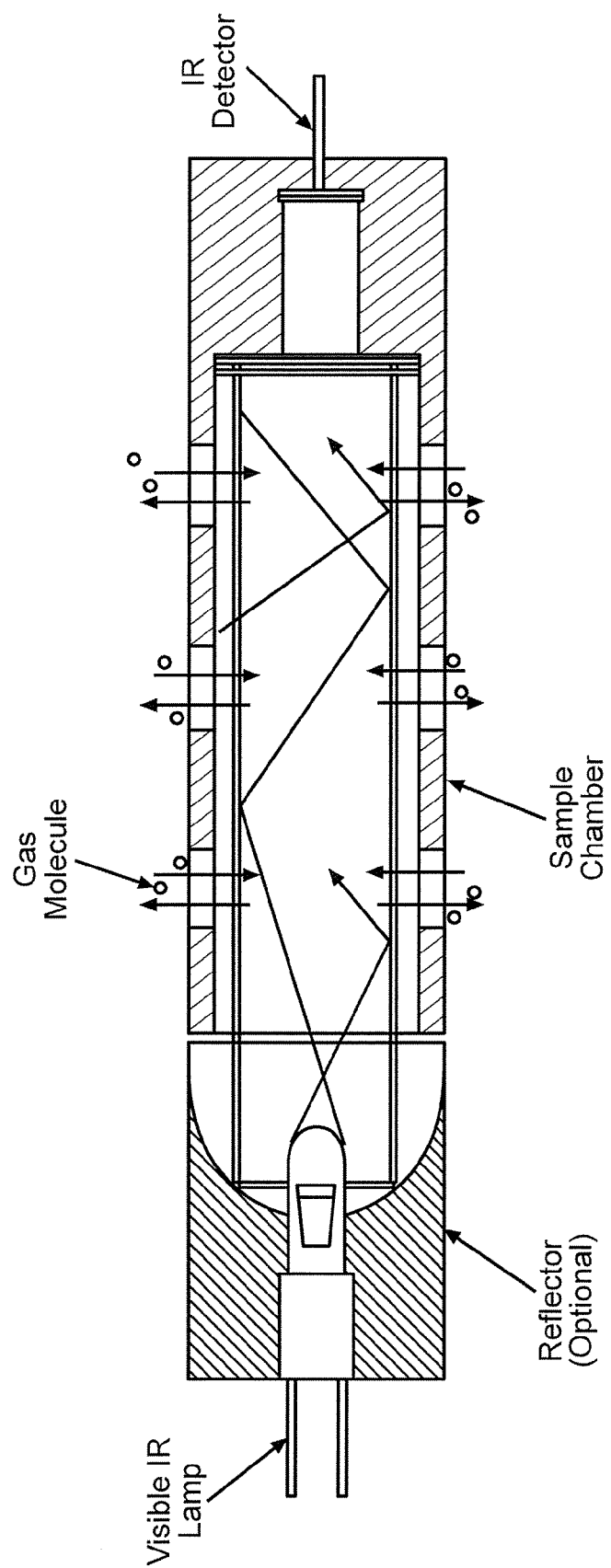
FIG. 6C is a diagrammatic view of an infra-red type gas sensor.
Figure 7A:
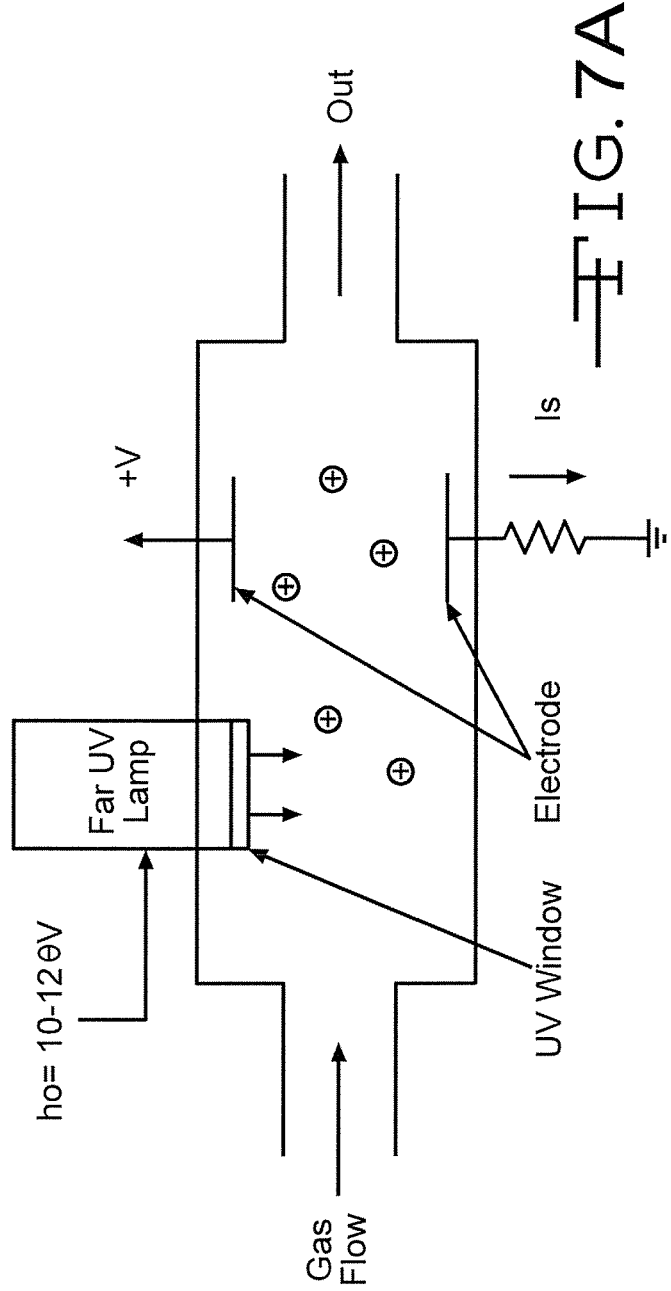
FIG. 7A is a diagrammatic view of a photo-ionization type gas sensor.

FIGS. 5A and 6C illustrate a gas sensor utilizing infra-red technology and FIG. 7A illustrates a gas sensor of the photo-ionization type. Gas sensors utilizing fluorescent technology have the following characteristics:
  UV light impinges on some organics produces a fluorescent light proportional to ambient gas concentration (e.g. oxygen).
  High sensitivity (because photo-detectors are sensitive).
  Applicable only to a few gases (but used with many biological materials where it can be sensitive and selective).
  Few commercial sensors using this technology are available.

Figure 11A:
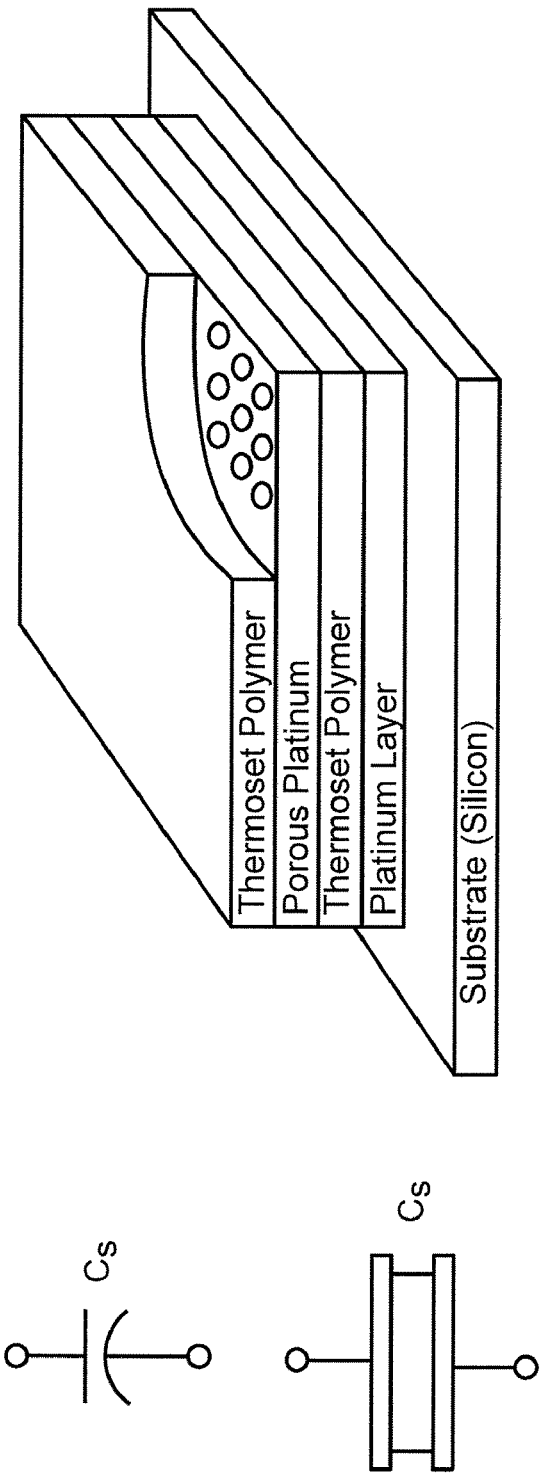
FIG. 11A is a diagrammatic view of a capacitive type gas sensor.

FIGS. 8A-10A illustrate a gas sensor of the surface acoustic wave (SAW) and vibrating beam type, and a capacitive type gas sensor is shown in FIG. 11A.

Other gas sensor technologies include polymer resistance, fiber optic, chemical field effect transistor (FET) and miniaturized versions of mass spectrometers. These technologies have resulted in few commercially available products. Micro electronic mechanical systems (MEMS) type gas sensors are miniaturized versions of types already described. They promise much smaller size, lower power and lower cost than conventional gas sensors. Many are under development but few are commercially available.

Appendix B

FIGS. 1B, 2B and 3B illustrate various shapes and electrical connections of electronic gas sensors.

The invention claimed is:

1. A signal conditioner for an electronic gas sensor comprising a sensor element and sensor specification information stored in digital form therewith, the signal conditioner comprising:
  a) an analog section for connection to the sensor element; and
  b) a digital section for connection to the stored sensor specification information and connected in controlling relation to the analog section;
  c) wherein the analog section includes a sensor excitation sub-section and a signal amplification sub-section;
  d) wherein the sensor excitation sub-section comprises:
    i) a switching regulator in the form of a dc-to-dc supply; and
    ii) a digital potentiometer for providing feedback to the switching regulator in response to input from the digital section; and
  e) so that the signal conditioner automatically adapts to a plurality of different electronic gas sensors and provides a digital output in a usable format.

2. The signal conditioner according to claim 1, wherein the sensor excitation sub-section comprises:
  a) a precision voltage reference; and
  b) a digitally controlled attenuation through which voltage from the reference is passed.

3. The signal conditioner according to claim 1, wherein the signal amplification sub-section comprises an amplifier having a low input bias current and a low input offset voltage.

4. The signal conditioner according to claim 1, wherein the digital section includes a microcontroller.

5. The signal conditioner according to claim 4, wherein the microcontroller has an analog-to-digital converter and provides a serial digital signal to the analog section.

6. The signal conditioner according to claim 1, wherein the digital section includes a microcontroller for reading the stored sensor specification information and for reconfiguring the analog section so that the signal conditioner matches the sensor specification information.

7. A signal conditioner for an electronic gas sensor comprising a sensor element and sensor specification information stored in digital form therewith, the signal conditioner comprising:
  a) an analog section for connection to the sensor element, the analog section including a sensor excitation sub-section and a signal amplification sub-section; and
  b) a digital section for connection to the stored sensor specification information and connected in controlling relation to the analog section, the digital section including a microcontroller for reading the stored sensor specification information and for reconfiguring the sensor excitation and signal amplification sub-sections for matching the signal conditioner to the sensor specification information;
  c) wherein the sensor excitation sub-section comprises:
    i) a switching regulator in the form of a dc-to-dc supply; and
    ii) a digital potentiometer for providing feedback to the switching regulator in response to input from the digital section;

d) so that the signal conditioner automatically adapts to a plurality of different electronic gas sensors and provides a digital output in a usable form.

8. The signal conditioner according to claim 7, wherein the sensor excitation sub-section comprises:
   a) a precision voltage reference; and
   b) a digitally controlled attenuation through which voltage from the reference is passed.

9. The signal conditioner according to claim 7, wherein the signal amplification sub-section comprises an amplifier having a low input bias current and a low input offset voltage.

10. An electronic gas sensor system comprising:
   a) an electronic gas sensor in the form of a plug-in module containing a sensor element and sensor specification information stored in digital form; and b) a signal conditioner comprising an analog section for connection to the sensor element, the analog section including a sensor excitation sub-section and a signal amplification sub-section and a digital section for connection to the stored sensor specification information and connected in controlling relation to the analog section, the digital section including a microcontroller for reading the stored sensor specification information and for reconfiguring the sensor excitation and signal amplification sub-sections for matching the signal conditioner to the sensor specification information;
   c) wherein the sensor excitation sub-section comprises:
      i) a switching regulator in the form of a dc-to-dc supply; and
      ii) a digital potentiometer for providing feedback to the switching regulator in response to input from the digital section;
   d) so that the plug-in module can be removed and replaced by another plug-in module containing a different sensor element and the signal conditioner automatically adapts to that another plug-in module and to a plurality of different electronic gas sensors and provides a digital output in a usable format.

11. The electronic gas sensor system according to claim 10, wherein the sensor excitation sub-section comprises:
   a) a precision voltage reference; and
   b) a digitally controlled attenuation through which voltage from the reference is passed.

12. The electronic gas sensor system according to claim 10, wherein the signal amplification sub-section comprises an amplifier having a low input bias current and a low input offset voltage.

13. A signal conditioning method for electronic gas sensors each comprising a sensor element, sensor specification information stored in digital form therewith, an analog section connected to the sensor element, wherein the analog section includes a sensor excitation subsection having a switching regulator in the form of a dc-to-dc supply, and a digital potentiometer, the method comprising:
   a) reading the sensor specification information;
   b) using the sensor specification information to establish sensor electrical parameters for signal conditioning applied to the sensor;
   c) using the digital potentiometer to provide feedback to the switching regulator in response to input from the digital section;
   d) reading data obtained from the sensor;
   e) using the sensor specification information to calculate and calibrate the data read from the sensor; and
   f) providing an output comprising data from the sensor in digital form.

14. The method according to claim 13, wherein a microcontroller is used to read the sensor specification information.

15. The method according to claim 13, wherein the sensor electrical parameters comprise sensor voltage, sensor current and sensor resistance.

16. The method according to claim 13, wherein the signal conditioning applied to the sensor comprises excitation and amplification.

* * * * *